United States Patent
Ahn et al.

(10) Patent No.: US 12,391,938 B2
(45) Date of Patent: Aug. 19, 2025

(54) BIO-INK SUPPLY SYSTEM AND THREE-DIMENSIONAL BIOPRINTING METHOD USING SAME

(71) Applicant: T&R BIOFAB CO., LTD., Siheung-si (KR)

(72) Inventors: Geun Seon Ahn, Seongnam-si (KR); Min Kyung Kim, Seongnam-si (KR); Kyung Hyun Min, Seongnam-si (KR); In Gyu Lee, Seongnam-si (KR); Dong Won Seok, Seongnam-si (KR)

(73) Assignee: T&R BIOFAB CO., LTD., Siheung-si (KR)

( * ) Notice: Subject to any disclaimer, the term of this patent is extended or adjusted under 35 U.S.C. 154(b) by 537 days.

(21) Appl. No.: 17/779,808

(22) PCT Filed: Dec. 13, 2019

(86) PCT No.: PCT/KR2019/017653
§ 371 (c)(1),
(2) Date: May 25, 2022

(87) PCT Pub. No.: WO2021/107250
PCT Pub. Date: Jun. 3, 2021

(65) Prior Publication Data
US 2022/0411779 A1 Dec. 29, 2022

(30) Foreign Application Priority Data
Nov. 26, 2019 (KR) .......... 10-2019-0153493
Nov. 26, 2019 (KR) .......... 10-2019-0153502

(51) Int. Cl.
*C12N 11/04* (2006.01)
*B33Y 10/00* (2015.01)
(Continued)

(52) U.S. Cl.
CPC .......... *C12N 11/04* (2013.01); *B33Y 10/00* (2014.12); *B33Y 30/00* (2014.12); *B33Y 40/10* (2020.01); *C12M 25/14* (2013.01)

(58) Field of Classification Search
CPC ......... C12N 11/04; B33Y 10/00; B33Y 30/00; B33Y 40/10; C12M 1/12; C12M 25/14
See application file for complete search history.

(56) References Cited

U.S. PATENT DOCUMENTS

| 10,874,999 | B2 * | 12/2020 | Ahn | ............. B01F 35/32005 |
| 2016/0067903 | A1 | 3/2016 | Chang et al. | |
| 2018/0127705 | A1 * | 5/2018 | Langenfeld | ............ C12M 27/18 |

FOREIGN PATENT DOCUMENTS

| CN | 101135814 A | 3/2008 | |
| CN | 100562788 | * 11/2009 | ........... G02F 1/1339 |

(Continued)

OTHER PUBLICATIONS

CN100562788 English translation prepared Oct. 11, 2024 (Year: 2024).*

(Continued)

*Primary Examiner* — Alison L Hindenlang
*Assistant Examiner* — Shibin Liang
(74) *Attorney, Agent, or Firm* — Studebaker Brackett PLLC

(57) ABSTRACT

Proposed is a bioink supply system and, more particularly, proposed is a bioink supply system including: a hydrogel storage part; cell storage part; a mixing part configured to receive and mix a hydrogel and a cell solution from the hydrogel storage part and the cell storage part; a sensor part configured to measure a level of bioink inside a syringe; and a controller configured to receive a signal from the sensor part and maintain a constant level of the bioink inside the syringe, in which the mixing part supplies, to the syringe, the bioink prepared by mixing the hydrogel and the cell solu- (Continued)

tion. The bioink supply system can continuously supply an active bioink to a syringe of a bioprinter during 3D bioprinting, and thus can continuously print large-scale biotissue, a plurality of organoids, organ-on-a-chip devices, etc.

9 Claims, 17 Drawing Sheets

(51) Int. Cl.
*B33Y 30/00* (2015.01)
*B33Y 40/10* (2020.01)
*C12M 1/12* (2006.01)

(56) References Cited

FOREIGN PATENT DOCUMENTS

| CN | 104972654 A | 10/2015 | |
|---|---|---|---|
| CN | 105196544 A | 12/2015 | |
| CN | 109228327 A | 1/2019 | |
| EP | 3561041 A1 | 10/2019 | |
| JP | H04-086439 A | 3/1992 | |
| JP | 2001-330303 A | 11/2001 | |
| JP | 2019-031094 A | 2/2019 | |
| KR | 10-0742631 B1 | 7/2007 | |
| KR | 10-2017-0111314 A | 10/2017 | |
| KR | 10-1799812 B1 | 11/2017 | |
| KR | 101795559 B1 | 11/2017 | |
| KR | 101800249 | * 11/2017 | ............ B01F 15/02 |
| KR | 10-1800249 B1 | 12/2017 | |
| KR | 10-2018-0042220 A | 4/2018 | |
| KR | 10-1852590 B1 | 4/2018 | |
| KR | 10-1975200 B1 | 5/2019 | |
| KR | 101992625 B1 | 6/2019 | |
| WO | 2006/020685 A2 | 2/2006 | |
| WO | 2017/209136 A1 | 12/2017 | |

OTHER PUBLICATIONS

CN100562788 English translation prepared Dec. 10, 2024 (Year: 2024).*
International Search Report issued in PCT/KR2019/017653; mailed Aug. 26, 2020.
An Office Action mailed by China National Intellectual Property Administration on Aug. 24, 2023, which corresponds to Chinese Patent Application No. 201980102483.7 and is related to U.S. Appl. No. 17/779,808.
The extended European search report issued by the European Patent Office on Oct. 26, 2023, which corresponds to European Patent Application No. 19954555.9-1103 and is related to U.S. Appl. No. 17/779,808.
An Office Action; "Notice of Reasons for Refusal," mailed by the Japanese Patent Office on Feb. 21, 2023, which corresponds to Japanese Patent Application No. 2022-530870 and is related to U.S. Appl. No. 17/779,808; with English language translation.

* cited by examiner

BIO-INK SUPPLY SYSTEM AND THREE-DIMENSIONAL BIOPRINTING METHOD USING SAME

CROSS-REFERENCE TO RELATED APPLICATIONS

This application is a National Phase Entry of U.S. Patent Application No. PCT/KR2019/017653 filed on Dec. 13, 2019, which claims benefit of priority to Korean Patent Application Nos. 10-2019-0153502 and 10-2019-0153493 both filed on Nov. 26, 2019, the entire content of which is incorporated herein by reference.

TECHNICAL FIELD

The present disclosure relates to generally to a bioink supply system. More particularly, the present disclosure relates to a bioink supply system capable of continuously supplying bioink by mixing a hydrogel and cells in real time during a three-dimensional (3D) bioprinting process, and to a 3D bioprinting method using the same.

Furthermore, the present disclosure relates generally to a 3D print head. More particularly, the present disclosure relates to a 3D print head capable of preventing dew condensation from occurring on a low-temperature head by improving thermal insulation performance of a high-temperature head, and to a 3D printer having the same.

Moreover, the present disclosure relates generally to a bio-clean bench system. More particularly, the present disclosure relates to a 3D printing system capable of performing 3D printing in a biologically stable environment, and to a 3D printing method using the same.

This work was supported by the Industrial Technology Innovation Program (No. 20000325) funded by the Ministry Of Trade, Industry & Energy (MI, Korea)).

BACKGROUND ART

Three-dimensional (3D) bioprinting refers to a technology that prints a specific shape by molding and stacking a shape desired by a user utilizing a bioprinter, bioink, cells, growth factors, etc.

With this 3D bioprinting technology, many studies have been actively conducted on an organoid, an organ-on-a-chip device, tissue and organ analogues for animal test replacement, etc. that can help in the healing of diseases. Bioink, a 3D bioprinting material, is a mixture of living cells capable of proliferation and differentiation, and a hydrogel such as collagen, gelatin, alginate, etc. which can maintain a specific shape or structure for a long period of time like human tissue. However, there is a difference between the survival conditions of the cells and the storage conditions of the hydrogel for bioprinting, so there is a limit to long-term storage of a large-capacity bioink prepared by mixing the cells and the hydrogel. In addition, conventional bioprinters can only accommodate a small amount of bioink in a syringe, so it is difficult to print a large-scale artificial organ or to continuously print a plurality of organoids, organ-on-a-chip devices, etc.

Meanwhile, 3D printing collectively refers to a technology for manufacturing a 3D structure by stacking a material composition for printing in a predetermined pattern using a 3D printer. In particular, 3D bioprinting is defined as a technology for 3D printing of biotissue using a biocompatible printing composition. With this 3D bioprinting system, many studies have been actively conducted on an organoid, an organ-on-a-chip device, tissue and organ analogues for animal test replacement, etc. that can help in the healing of diseases. The printing composition used for 3D bioprinting is based on a hydrogel, a thermoplastic polymer, etc., and may include cells or growth factors.

When manufacturing a 3D structure such as an organoid, an organ-on-a-chip device, tissue and organ analogues for animal test replacement through such a 3D bioprinting system, a multi-head capable of jetting or printing a biocompatible printing composition such as a hydrogel and a thermoplastic polymer composition together are used in many cases. In order to perform 3D printing using a printing composition based on a hydrogel, a thermoplastic polymer, etc., it is necessary for the printing composition to be maintained in a liquid phase with flowability so that it can be jetted from a 3D print head.

A printing composition containing a thermoplastic polymer has to be maintained at a high temperature in the 3D print head for jetting or printing so that it can be maintained in a semi-solid phase, which is a liquid phase with flowability, in the 3D print head. In this case, due to a temperature difference between the inside and outside of the 3D print head, water contained in external air may condense on the surface of the print head, causing dew condensation.

In addition, in order to perform 3D printing using a biocompatible printing composition such as a hydrogel, it is necessary for the composition to be maintained at room temperature or a lower temperature in the 3D print head so that it does not undergo a phase change and can be maintained in a liquid phase with flowability suitable for printing. In this case, due to a temperature difference between the inside and outside of the 3D print head, water contained in external air may condense on the surface of the print head, causing dew condensation.

Therefore, in the case of the multi-head with 3D print heads that use a plurality of different materials, there is a possibility that such a difference in use temperature range causes water contained in external air to condense on the surface of the print heads and results in dew condensation. The occurrence of dew condensation is very fatal in 3D bioprinting in which a clean printing environment is required because condensed water tends to capture contaminants from the surrounding environment. In addition, if water condensed on the surface of the 3D print heads collects and forms droplets, it may fall onto a printed material being printed, which is problematic.

In fact, as illustrated in FIG. 1, when 3D print heads maintained at different temperatures are arranged adjacent to each other (due to the internal structure of a 3D printer), heat emitted from the print head maintained at a relatively high temperature (16° C.) causes dew condensation on the outer peripheral surface of the print head operated at a relatively low temperature (4° C.) (the dew point temperature of a clean room where the 3D printer is located is about 9° C.)

Conventionally, for the purpose of temperature control to avoid such dew condensation, a fan was mounted on the rear side of the 3D print heads to cool the 3D print heads. However, in the case of controlling the temperature with the fan, the temperature of the 3D print heads as well as the temperature of the entire 3D printing space is changed, so the problem of dew condensation still exists. Also, due to the operation of the fan for temperature control, contaminants around the 3D printer may be concentrated on a printed material being printed.

A bioprinting composition used in 3D bioprinting is a 3D printing material including cells, growth factors, etc. on the basis of a hydrogel, etc. For the survival of the cells included in the bioprinting composition, it is necessary that the 3D bioprinting environment is maintained in a sterile state, and temperature and humidity are maintained constant. In general, a clean 3D bioprinting environment can be created by disposing a 3D bioprinter in a clean room, but this is costly and requires special authentication facilities. In addition, even when clean air is supplied through the clean room, a stagnant area occurs due to the flow of air (airflow), and contaminants such as fine particles are collected in the stagnant area, causing a printing result to be physically or biologically contaminated.

DISCLOSURE

Technical Problem

An objective of the present disclosure is to provide a bioink supply system capable of continuously supplying an active bioink to a syringe of a bioprinter during three-dimensional (3D) bioprinting, to provide a 3D bioprinting method using the same.

Another objective of the present disclosure is to provide a 3D print head having a cover made of a polymer material with very low thermal conductivity so as to exhibit excellent thermal insulation performance, thereby preventing dew condensation from occurring on a 3D print head operated at a low temperature, and to provide a 3D printer and a 3D printing system having the same.

Still another objective of the present disclosure is to provide a bio-clean bench system capable of obtaining an uncontaminated and stable result by performing operation of a driving device (e.g., 3D printing, etc.) in a clean, biologically stable environment without requiring the use of expensive clean room equipment, and to provide a driving method thereof.

Technical Solution

According to one aspect of the present disclosure there is provided a bioink supply system including: a hydrogel storage part (1100); a cell storage part (1200); a mixing part (1300) receiving and mixing a hydrogel and a cell solution from the hydrogel storage part (1100) and the cell storage part (1200); a sensor part (1500) measuring the level of bioink inside a syringe (1400); and a controller (1600) receiving a signal from the sensor part (1500) and maintaining a constant level of the bioink inside the syringe (1400), in which the mixing part (1300) may supply, to the syringe (1400), the bioink prepared by mixing the hydrogel and the cell solution.

The hydrogel storage part (1100) may include a pH adjusting means, and the cell storage part (1200) may include a stirring means.

In addition, the cell storage part (1200) may be maintained under conditions of $CO_2$ concentration of 5%, temperature of 37° C., and pH of 7 to 7.5.

The mixing part (1300) may include an impeller as a mixing means (1310), and the sensor part (1500) may include a laser sensor or a stretch sensor (1510).

Meanwhile, according to another aspect of the present disclosure, there is provided a three-dimensional bioprinting method including: storing a hydrogel in a hydrogel storage part (1100); storing a cell solution containing live cells in a cell storage part (1200); supplying the hydrogel and the cell solution from the hydrogel storage part (1100) and the cell storage part (1200) to a mixing part (1300); mixing the hydrogel and the cell solution in the mixing part (1300) and supplying the mixture to a syringe (1400); and maintaining a constant level of bioink inside the syringe (1400).

The hydrogel may include alginate, fibrinogen, carboxymethyl cellulose, heparan sulfate, hyaluronic acid, collagen, or dextran.

The storing of the hydrogel may be performed under conditions of temperature of 10° C. to 15° C. and pH of 5 to 6, and the storing of the cell solution may be performed under conditions of $CO_2$ concentration of 5%, temperature of 37° C., and pH of 7 to 7.5.

According to another aspect of the present disclosure, there is provided a three-dimensional (3D) print head including: a syringe (100) accommodating a printing composition (1) therein and jetting the printing composition (1) through a nozzle (150) at a lower portion thereof; a heating block (120) formed on an outer peripheral surface of the syringe (100); and a cover (130) formed to surround the heating block.

The printing composition (1) may include a thermoplastic polymer, and the cover (130) may be an engineering plastic or a ceramic material having excellent thermal insulation and heat resistance properties.

In addition, the cover (130) may have a prefabricated structure including: a main cover (131) accommodating the heating block (120) therein; an upper cover (132) coupled to an upper end of the main cover (131) to surround an upper end of the heating block (120); and a lower cover (133) coupled to a lower end of the main cover (131) to surround a lower end of the heating block (120), or may have an integral structure in which these elements are formed into a single body.

In addition, the thickness of the cover (130) may be in the range of 1 to 10 mm, and a cartridge heater heating the heating block (120) may include a hot wire, a thermocouple element, or a Peltier element.

According to still another aspect of the present disclosure, there is provided a multi-3D print head including: the above-described 3D print head as a high-temperature head (160); and as a low-temperature head (170), a syringe (101) accommodating a hydrogel therein and jetting the hydrogel through a nozzle at a lower portion thereof.

A moisture absorber (141) may be further provided on an outer peripheral surface of the syringe (101) constituting the low-temperature head (170). The moisture absorber (141) may include a wool or cotton material having excellent absorbency, or silica gel, calcium chloride, or zeolite.

In addition, the moisture absorber (141) may be detachably attached to the outer peripheral surface of the syringe (101) by means of a magnet, Velcro, or bolt fastening.

According to still another aspect of the present disclosure, there is provided a multi-head 3D printer including: a high-temperature head (160) including a syringe (100) accommodating a printing composition (1) therein and jetting the printing composition (1) through a nozzle (150) at a lower portion thereof, a heating block (120) formed on an outer peripheral surface of the syringe (100), and a cover (130) formed to surround the heating block; and a low-temperature head (170) including a syringe (101) accommodating a hydrogel therein and jetting the hydrogel through a nozzle at a lower portion thereof, and a moisture absorber (141) attached to an outer peripheral surface of the syringe (101), in which heat may be transferred to the inside of the syringe (100) through the heating block (120), and the heat may be blocked from being emitted to the outside by the cover (130).

Moreover, the present disclosure may further include a 3D bioprinting system for three-dimensionally printing a biotissue using the multi-head 3D printer described above.

According to still another aspect of the present disclosure, there is provided a clean bench system including: a housing; an air supply unit supplying air into the housing; a driving device located inside the housing; and an airflow guide formed to cover the driving device to control an airflow of supplied air.

The driving device may be at least one selected from the group consisting of a 3D printer, a stirring device, an incubator, and an automatic pipette device accompanied by mechanical operation or movement. A plurality of surfaces constituting the airflow guide may form an angle of equal to or less than 90 degrees with the direction of the airflow of supplied air, and may guide the direction of the supplied airflow from the air supply unit downwards, thereby removing a stagnant area of the airflow.

The air supply unit may include an air supply port formed in a lower portion of the air supply unit, and a filter installed in the air supply port. The clean bench system according to the present disclosure may further include a temperature and humidity adjustment unit supplying air whose temperature or humidity is adjusted to the air supply unit.

In addition, the housing may be provided with a transparent window so that the inside of the housing can be viewable from the outside. As the filter, a high efficiency particulate air filter (HEPA filter) or a pre-filter may be used.

The airflow guide may include a stage cover covering a stage of a 3D printer, or a cable cover covering a cable of the 3D printer. The cable cover may be slid through a rail structure in conjunction with forward and backward movement of the airflow guide.

According to a modified aspect of the present disclosure, there is provided a clean bench system driving method including: a temperature and humidity control step of supplying air whose temperature and humidity are adjusted by a temperature and humidity adjustment unit to an air supply unit; an air supply step of filtering the air supplied to the air supply unit with a filter and supplying the filtered air into a housing; and an air discharging step of discharging the air supplied to the inside of the housing through a vent formed in a lower portion of the housing. An airflow of the air supplied through the air supply unit may be controlled by an airflow guide formed to cover a driving device located inside the housing.

Advantageous Effects

A bioink supply system according to the present disclosure can continuously supply an active bioink to a syringe of a bioprinter during 3D bioprinting, and thus can continuously print large-scale biotissue, a plurality of organoids, organ-on-a-chip devices, etc.

In addition, it is possible to maintain a constant level of the bioink inside the syringe during bioprinting, thereby enabling precise bioprinting.

A multi-3D print head according to the present disclosure has a cover made of a polymer having very low thermal conductivity and excellent heat resistance on a high-temperature head. Thus, it is possible to prevent dew condensation on the surface of a low-temperature head used together with the high-temperature head and thus maintaining a clean 3D printing environment.

In addition, the cover according to the present disclosure can suppress heat inside the 3D print head from being emitted to the outside, so it is possible to lower the power consumption for maintaining a constant temperature inside the 3D print head.

A clean bench system according to the present disclosure can provide an aseptic environment without requiring the use of expensive clean room equipment.

The clean bench system according to the present disclosure includes an airflow guide to facilitate the flow (airflow) of supplied air. Thus, it is possible to effectively prevent a driving device located in a housing, particularly a 3D printing system, from being contaminated by stagnant fine particles (contaminants).

In addition, the clean bench system according to the present disclosure accommodates the 3D printing system therein and enables temperature and humidity adjustment and contamination source control. Thus, it is possible to stably perform a 3D bioprinting process in a biologically stable environment.

Figure 1:
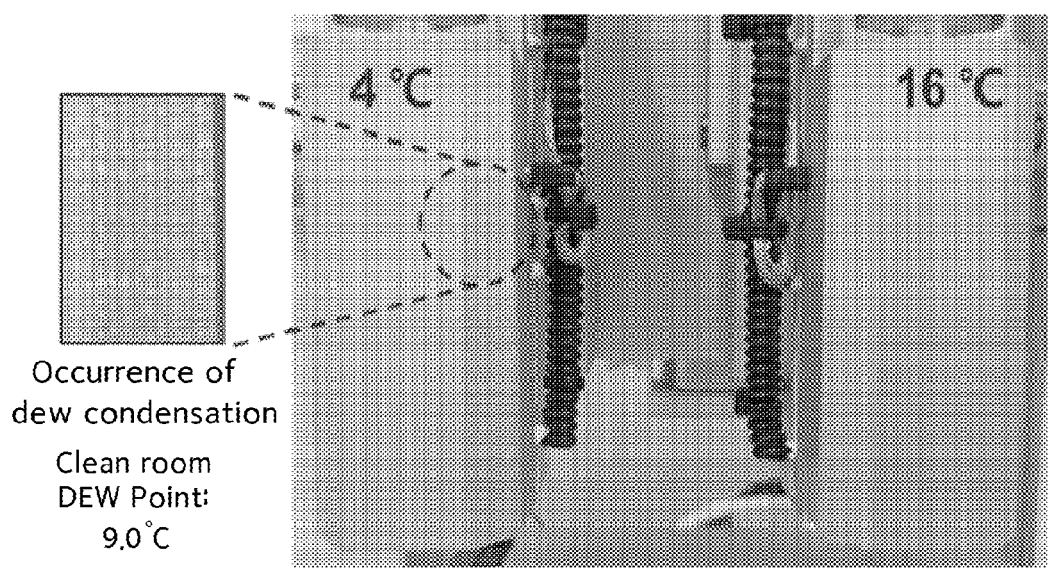
FIG. 1 is an image illustrating an example in which dew condensation occurs in a multi-3D print head according to the related art.

| [Description of the Reference Numerals in the Drawings] | |
| --- | --- |
| 1: printing composition | 3: head |
| 4: head moving unit | 5: stage |
| 100: syringe | 120: heating block |
| 130: cover | 131: main cover |
| 132: upper cover | 133: lower cover |
| 134: first coupling hole | 135: first through-hole |
| 136: second coupling hole | 137: second through-hole |
| 138: nozzle cover | 140: receiving portion |
| 141: moisture absorber | 150: nozzle |
| 160: high-temperature head | 170: low-temperature head |
| 180: composite head | 310: housing |
| 311: transparent window | 313: vent |
| 320: air supply unit | 321: air supply port |
| 323: filter | 325: suction port |
| 330: 3D printer | 340: airflow guide |
| 343: stage cover | 345: cable cover |
| 350: temperature and humidity adjustment unit | |
| 351: casing | |
| 353: inlet | 355: outlet |
| 1100, 1101, 1102, 1103, 1104, 1105, and 1106: hydrogel storage part | |
| 1200, 1201, 1202, 1203, 1204, 1205, and 1206: cell storage part | |
| 1300, 1301, 1302, 1303, 1304, 1305, and 1306: mixing part | |
| 1310: mixing means | 1320: pump |
| 1400, 1401, 1402, and 1403: syringe | 1500: sensor part |
| 1510: stretch sensor | 1520: sensor cable |
| 1530: cap | 1600: controller |
| 1700, 1701, and 1702: 3D bioprinter | 1710: support |
| 1720: head moving unit | 1730: x-axis stage |

MODE FOR INVENTION

Hereinbelow, exemplary embodiments of the present disclosure will be described in detail with reference to the accompanying drawings. All terms or words used herein should not be interpreted as being limited merely to common and dictionary meanings but should be interpreted as having meanings and concepts which are defined within the technical scope of the present disclosure.

It will be further understood that the terms "comprise", "include", and/or "have", when used herein, specify the presence of elements but do not preclude the presence or addition of other elements unless specified otherwise. Also, the term "part" when used herein means a unit or block for performing a specific function.

Respective steps may be performed in a sequence different from that described unless a particular sequence is specified. That is, the steps may be performed in the sequence described and substantially simultaneously, but they may be performed in reverse direction.

Hereinafter, a bioink supply system and a three-dimensional (3D) bioprinting method using the same according to the present disclosure will be described in more detail.

The present disclosure relates to a 3D print head for accommodating or jetting a printing composition, among components of a 3D printer. In particular, the present disclosure relates to a head structure capable of effectively preventing dew condensation from occurring on the surface of a multi-3D print head operated in different temperature ranges, and to a 3D printer having the same, and to a 3D printing system. A description of other components of the 3D printer unnecessary in describing the present disclosure will be omitted herein.

Hereinafter, a 3D print head capable of preventing dew condensation with improved thermal insulation performance according to the present disclosure will be described in more detail.

Figure 2:
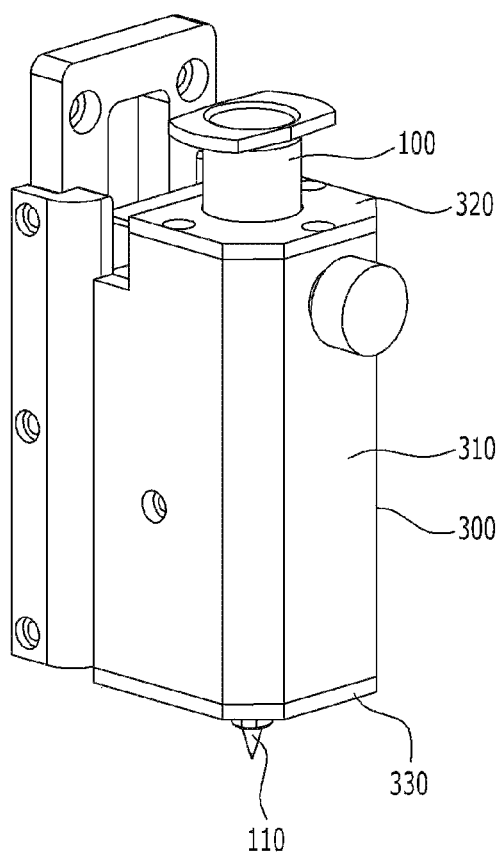
FIG. 2 is a perspective view illustrating a high-temperature head (160) for a 3D printer according to an embodiment of the present disclosure.
Figure 3:
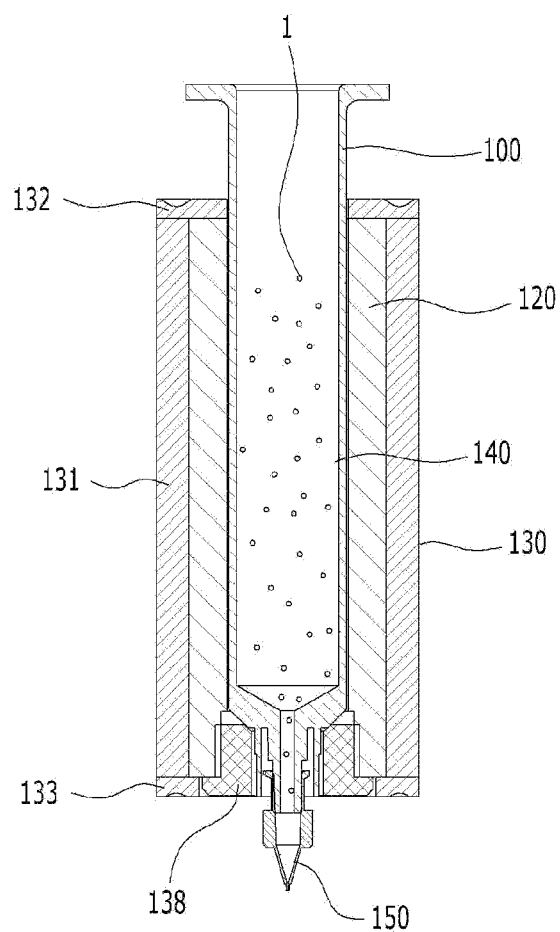
FIG. 3 is a sectional view illustrating the high-temperature head (160) for the 3D printer according to the embodiment of the present disclosure.
Figure 4:
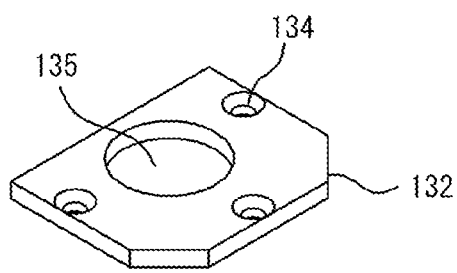
FIG. 4 is an exploded view illustrating a cover (130) used in the high-temperature head (160) of the present disclosure.
Figure 4:
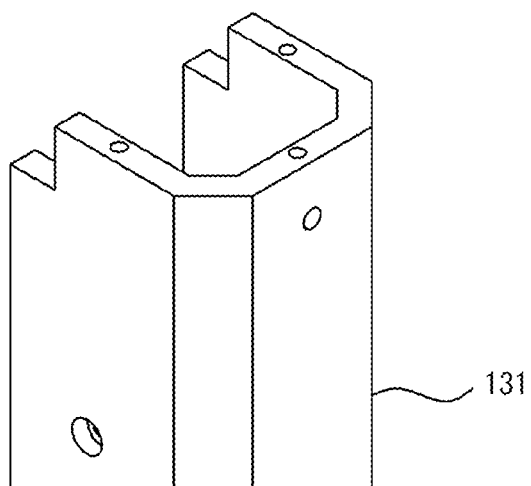
Figure 4:
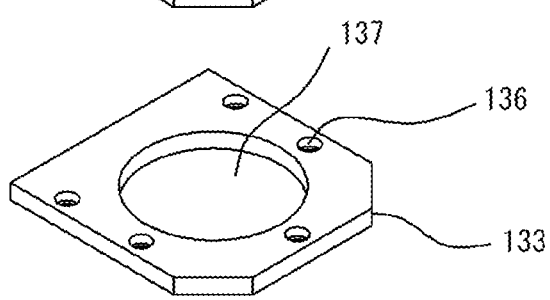

FIG. 2 is a perspective view illustrating a high-temperature head 160 for a 3D printer according to an embodiment of the present disclosure. FIG. 3 is a sectional view illustrating the high-temperature head 160 for the 3D printer according to the embodiment of the present disclosure.

Referring to FIGS. 2 and 3, the high-temperature head 160 for the 3D printer according to the embodiment of the present disclosure includes: a syringe 100 for jetting a printing composition 1; a heating block 120 formed on an outer peripheral surface of the syringe 100; and a cover 130 formed to surround the heating block 120.

The high-temperature head 160 for the 3D printer according to the present disclosure may jet the printing composition 1 while being moved by a driving device and a control device of the 3D printer.

As illustrated in FIG. 3, the syringe 100 includes a receiving portion 140 accommodating the printing composition 1 therein, and a nozzle 150 jetting the printing composition 1 accommodated in the receiving portion 140.

The printing composition 1 may include a thermoplastic polymer. The thermoplastic polymer may include, but is not limited to, a polymer that can have flowability like fluid through heating, for example, at least one selected from the group consisting of 3D-printable materials, such as lactide, caprolactone, glycolide, dioxanone, propylene, ethylene, vinyl chloride, butadiene, methyl methacrylate, acrylic acid, 2-hydroxyethyl methacrylate, carbonate, and polyethylene terephthalate, acrylonitrile butadiene styrene (ABS), polycaprolactone (PCL), acrylonitrile-styrene-acrylate (ASA), styrene-acrylonitrile copolymer (SAN), polystyrene (PS), polyphenylsulfone (PPSF/PPSU), polyetherimide, polylactic acid (PLA), poly-d-lysine (PDL), etc.

In order for the printing composition 1 to be jetted through the nozzle 150, the printing composition 1 has to be maintained in a liquid phase with flowability, such as a semi-solid phase. To this end, the temperature of the printing composition 1 has to be maintained above a predetermined temperature. The heating block 120 transfers heat to the syringe 100 so that the printing composition 1 accommodated in the receiving portion 140 of the syringe 100 is maintained in a semi-solid phase like fluid.

The heating block 120 is preferably formed on the outer peripheral surface of the syringe 100 so as to evenly transfer heat to the printing composition 1 accommodated in the syringe 100. The heating block 120 is heated by receiving heat from a cartridge heater mounted on a rear surface thereof, and is preferably made of an aluminum material having excellent thermal conductivity. The cartridge heater may include a heating wire, a thermocouple element, or a Peltier element.

The cover 130 blocks the heat generated by the heating block 120 from being transferred to the outside, thereby preventing dew condensation from occurring in another 3D print head operated at a relatively low temperature, and is preferably made of a material having very low thermal conductivity and excellent heat resistance that can withstand high temperatures.

The material used for the cover 130 may include at least one selected from the group consisting of heat-resistant engineering plastics or ceramics, such as polyetheretherketone (PEEK), polytetrafluoroethylene (PTFE), polyimide (PI), polyphenylene sulfide (PPS), and polyethersulfone (PES), preferably polyetheretherketone.

Polyetheretherketone (PEEK) has excellent heat resistance and processability and has a very low thermal conductivity of about 0.25 W/mk, and thus is suitable to prevent the heat generated by the heating block 120 from being transferred to the outside.

As illustrated in FIG. 3, the cover 130 may include: a main cover 131 accommodating the heating block 120 therein; an upper cover 132 coupled to an upper end of the main cover 131 to surround an upper end of the heating block 120; and a lower cover 133 coupled to a lower end of the main cover 131 to surround a lower end of the heating block 120. As described above, by forming the cover 130 in a separated type, it is possible to facilitate processing of the cover 130 and lower processing costs.

In addition, the main cover 131, the upper cover 132, and the lower cover 133 constituting the cover 130 may be integrally formed in a single body.

In the case of the separated-type cover 130, the upper cover 132 may include a first coupling hole 134 formed in an outer surface of the upper cover 132 and a first through-hole 135 formed in the center of the upper cover 132 and through which the syringe 100 passes. The main cover 131 and the upper cover 132 may be coupled to each other by means of screw coupling through the first coupling hole 134, or may be coupled to each other by means of an adhesive such as an epoxy resin that can be used at a high temperature. In addition, the lower cover 133 may include a second coupling hole 136 formed in an outer surface of the lower cover 133 and a second through-hole 137 formed in the center of the lower cover 133 and through which the syringe 100 passes. Similar to the upper cover 132, the main cover 131 and the lower cover 133 may be coupled to each other by means of screw coupling through the second coupling hole 136, or may be coupled to each other by means of an adhesive such as a resin that can be used at a high temperature. When screw coupling is used, it is preferable to use a screw made of the same material as the cover 130 in order to maximize a thermal insulation effect.

The thickness of the cover 130 is not particularly limited, but is preferably in the range of 1 to 10 mm, and it is advantageous in terms of thermal insulation performance when the thickness is larger than at least 1 mm. However, when considering a precise movement of the head, a thickness exceeding 10 mm is not preferable because it may deteriorate precision of a printed material.

In addition, as illustrated in FIG. 3, the cover 130 may further include a nozzle cover 138 extending from the lower cover 133 and formed between the heating block 120 and the nozzle 150. The nozzle cover 138 blocks heat of the nozzle 150 from being transmitted to the outside to maintain a constant temperature inside the nozzle 150, and prevents dew condensation from occurring in the nozzle 150.

The main cover 131, the upper cover 132, the lower cover 133, and the nozzle cover 138, which constitute the cover 130, may be configured, if necessary, in the form of a hollow structure having an empty space therein to utilize an air layer with an excellent thermal insulation effect.

Figure 5:
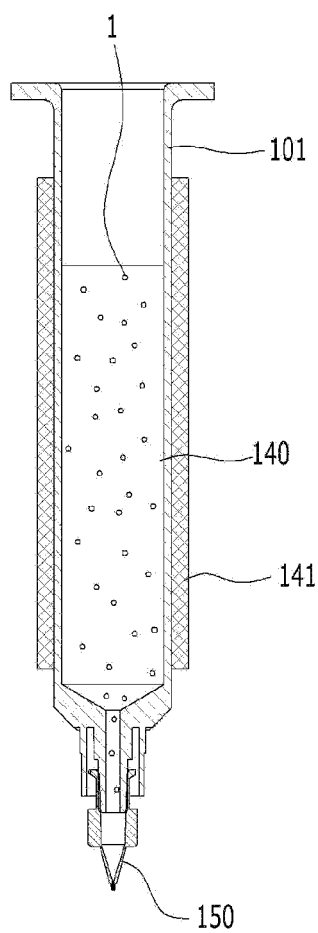
FIG. 5 is a sectional view illustrating a low-temperature head (170) for the 3D printer according to the embodiment of the present disclosure.

In addition, a multi-3D print head according to the present disclosure may include a low-temperature head 170 illustrated in FIG. 5 together with the high-temperature head 160. As illustrated in FIG. 5, the low-temperature head 170 for 3D printing includes a syringe 101 accommodating a hydrogel therein and jetting the hydrogel through a nozzle at a lower portion thereof, and may further include a moisture absorber 141 capable of absorbing dew condensation occurring on the surface of the head.

The hydrogel may include at least one selected from the group consisting of alginate, fibrinogen, carboxymethyl cellulose, heparan sulfate, hyaluronic acid, collagen, and dextran.

The moisture absorber 141 may be formed in a form in which a hygroscopic material is coated on the outer peripheral surface of the syringe 101 of the low temperature head 130 or is detachably attached thereto, and absorbs dew condensation to prevent it from falling onto a printed material being 3D printed.

As the hygroscopic material included in the moisture absorber 141, silica gel, calcium chloride ($CaCl_2$)), zeolite, etc. may be used, or wool, cotton, etc. having excellent absorbency may be used. When the moisture absorber 141 is coupled to the outer peripheral surface of the syringe 101 in a detachable form, it is preferably attached to the outer peripheral surface of the syringe 101 by means of a magnet, Velcro, or bolt fastening. In this case, a plurality of moisture absorbers 141 may be attached to the outer peripheral surface of the syringe 101.

The multi-3D print head according to the present disclosure may include both the high-temperature head 160 and the low-temperature head 170 simultaneously, and can be effectively applied to a 3D printer and a 3D printing system having such a multi-head structure. Also, it is possible to effectively prevent the occurrence of dew condensation caused by a temperature difference between each head and to minimize the contamination of a final 3D structure. Thus, the present disclosure is more useful in a 3D bioprinting system for 3D printing of biotissue.

Example

A heating block was formed on an outer peripheral surface of a syringe for jetting a printing composition, after which a cover was formed to a thickness of 3 mm with polyetheretherketone to surround the heating block. Thereby, a high-temperature head for a 3D printer was manufactured.

Comparative Example

A heating block was formed on an outer peripheral surface of a syringe for jetting a printing composition, and thereby, a high-temperature head for a 3D printer without a separate cover was manufactured.

Experimental Example 1: Measurement of Thermal Insulation Performance

To measure the thermal insulation performance of the 3D print head according to the present disclosure, after setting temperatures of the heating blocks of the Example and the Comparative Example to 100° C., and surface temperature of the cover of the Example and surface temperature of the heating block of the Comparative Example were measured for 1 hour. The results are illustrated in FIG. 6.

Figure 6:
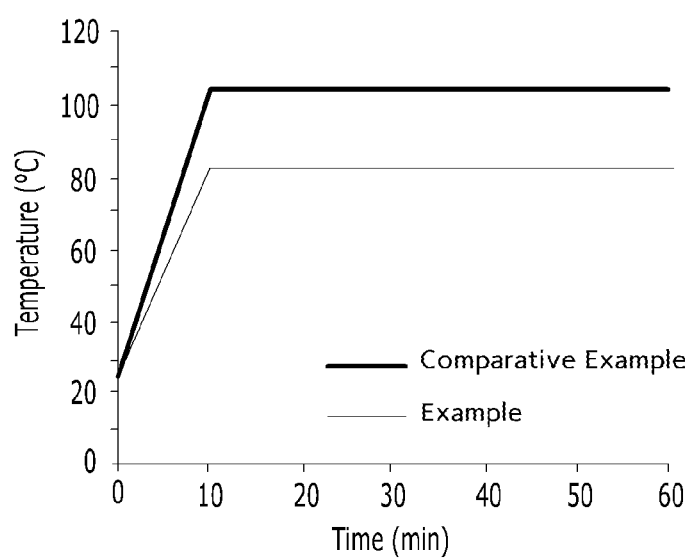
FIG. 6 is a graph illustrating the results of measuring the thermal insulation performance of a 3D print head according to the embodiment of the present disclosure.

With reference to the results illustrated in FIG. 6, in the case of the Comparative Example, the temperature was increased from an initial temperature of 23.8° C. to 103.9° C. for 10 minutes, which latter was then maintained constant. On the other hand, in the case of the Example, the temperature of 24.7° C. to 81.9° C. for 10 minutes, which latter was then maintained constant. This confirmed that in the case of the Example including the cover, a thermal insulation effect of about 20° C. was achieved.

Figure 7:
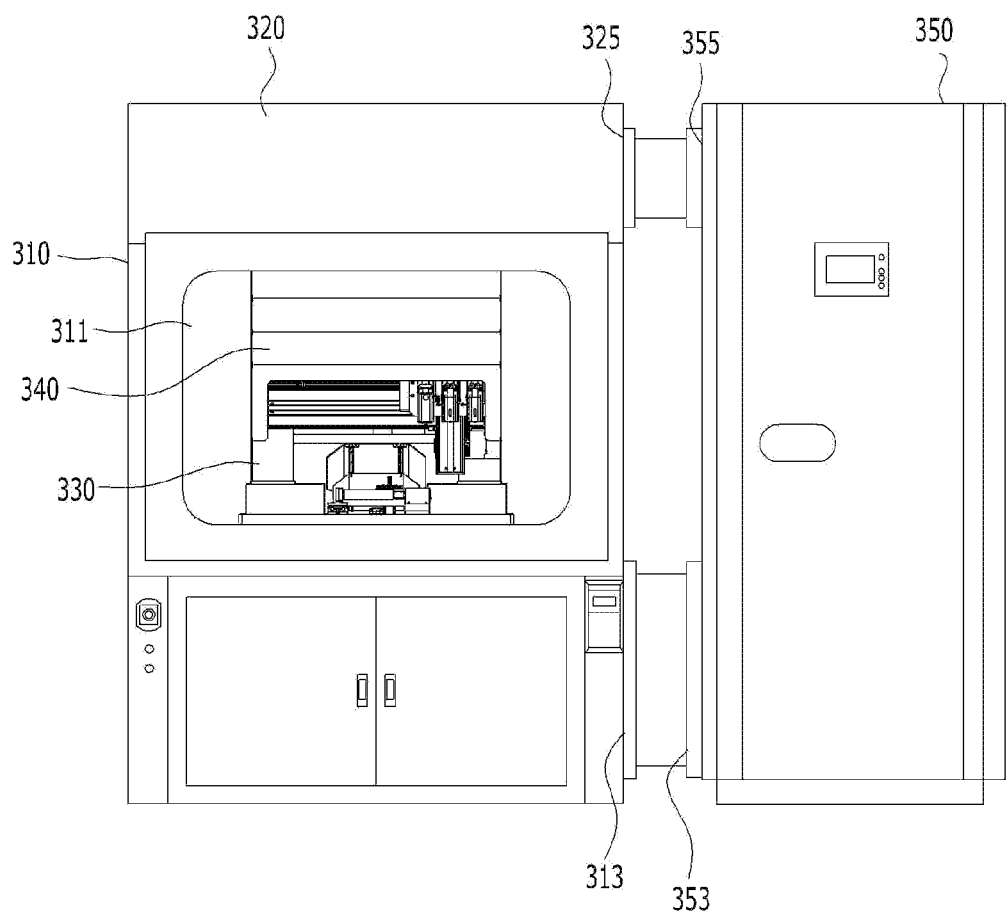
FIG. 7 is a perspective view illustrating a clean bench system according to another embodiment of the present disclosure.
Figure 8:
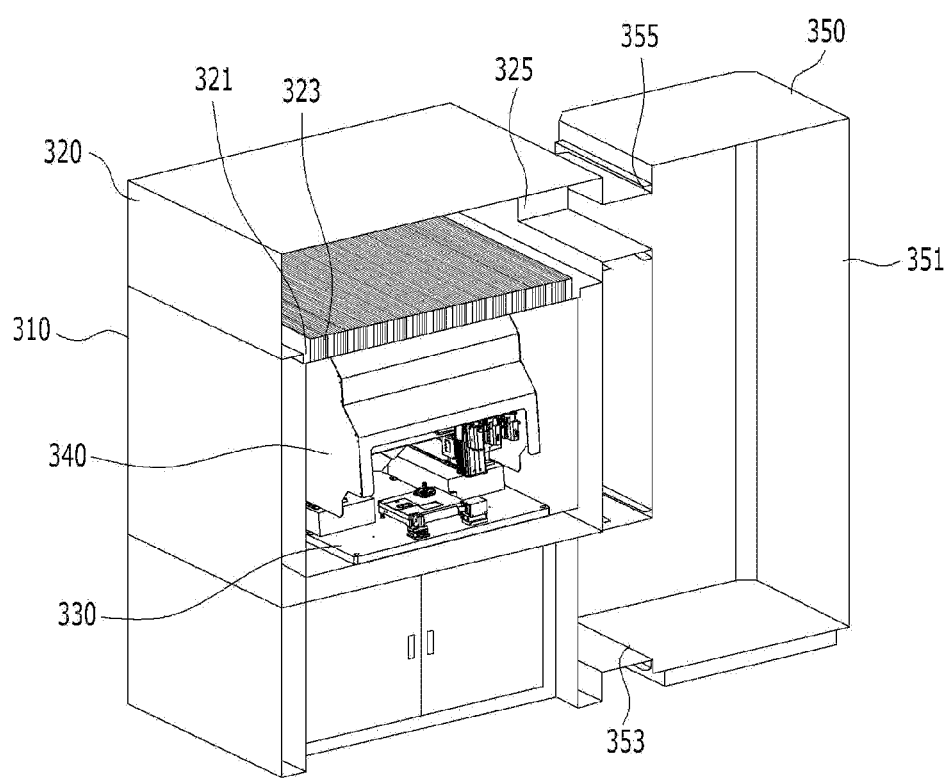
FIG. 8 is a view illustrating the inside of the clean bench system according to the other embodiment of the present disclosure.

FIG. 7 is a perspective view illustrating a clean bench system according to another embodiment of the present disclosure. FIG. 8 is a view illustrating the inside of the clean bench system according to the other embodiment of the present disclosure.

Referring to FIGS. 7 and 8, the clean bench system according to the present disclosure includes: a housing 310; an air supply unit 320 formed on the housing 310 and supplying air into the housing 310; a 3D printer 330 serving as a driving device provided inside the housing 310; an airflow guide 340 formed to cover the 3D printer 330; and a vent 313 formed in a lower portion of the housing 310.

The housing 310 provides a clean area in a clean bench, and may accommodate a driving device such as the 3D printer 330 therein. Although the 3D printer has been described as an example of the driving device, any driving mechanism that has mechanical movement within the clean bench may be included without any particular limitation. Examples include various experimental devices such as a 3D printer, an automatic pipette device, a stirrer, and an incubator, and more preferably, a 3D printer capable of precisely controlling the shape and structure of a printing result.

The housing 310 may be made of various metal materials such as steel, stainless steel, aluminum, titanium, etc. The shape of the housing 310 is not particularly limited as long as it has a shape that can surround the driving device. For example, the shape of the housing 310 may be a cylinder, a cube, or a cuboid.

In the housing 310, a transparent window 311 through which the inside of the housing 310 is viewable from the outside may be formed. Through the transparent window 311, the 3D printer 330, serving as the driving device installed inside the housing 310, may be checked, or the operating state of the 3D printer 330 may be checked. The transparent window 311 may be made of a transparent material such as glass or plastic.

The air supply unit 320 supplies air into the housing 310, and is formed on the housing 310. The air supplied through the air supply unit 320 is discharged to the outside of the housing 310 through the vent 313 formed in the lower portion of the housing 310. In this manner, the clean bench system according to the present disclosure guides the flow of air in one direction (i.e., in a vertical direction from top to bottom of the housing) to cross the 3D printer 330 serving as the driving device.

The air supply unit 320 includes a suction port 325 sucking air from the outside of the housing 310, a supply port 321 supplying the sucked air from the suction port 325 into the housing 310; and a filter 323 installed in the supply port 321.

As the filter 323, a high efficiency particulate air filter (HEPA filter) or a pre-filter may be used, preferably a HEPA filter class EU10 having an efficiency of 95% to 99.9%, and more preferably a HEPA filter class U17 having an efficiency of 99.999995%. By filtering the air outside the housing 310 through the filter 323 and supplying the filtered air to the inside of the housing 310, the environment inside the housing 310 can be maintained clean.

The 3D printer 330, which is a representative driving device, may be provided inside the housing 310, which is a space in which a clean environment is maintained, and may be formed integrally with the housing 310 or may be formed separately from the housing 310 to be detachably attached thereto.

Figure 9:
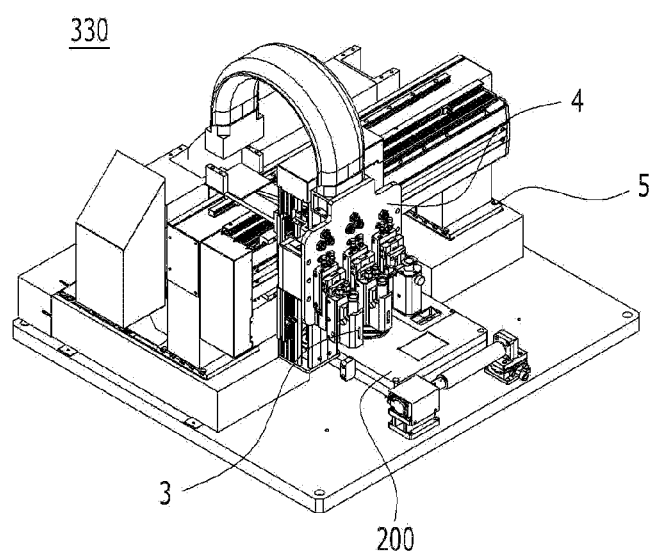
FIG. 9 is a perspective view illustrating a 3D printer that is accommodated in the clean bench system according to the other embodiment of the present disclosure.

As illustrated in FIG. 9, the 3D printer 300 may include: a print head 3 jetting a printing composition 1; a support plate 200 on which the jetted printing composition 1 is stacked; a head moving unit 4 moving the print head 3; and a stage 5 guiding movement of the head moving unit 4.

The print head 3 jets the printing composition 1 while being moved along the stage 5 by the head moving unit 4 to print a 3D structure. In this case, the printing composition 1 may be jetted from the print head 3 to the support plate 200 by means of pneumatic pressure. A jet amount and jet speed of the printing composition 1 to be jetted may be adjusted by appropriately controlling the pneumatic pressure according to the concentration of the printing composition 1 and the diameter of a nozzle of the print head 3.

The printing composition 1 may include a thermoplastic polymer, a hydrogel, or a mixture thereof, and may further include cells in addition to the thermoplastic polymer or hydrogel if necessary.

The thermoplastic polymer may include, but is not limited to, for example, at least one selected from the group consisting of lactide, caprolactone, glycolide, dioxanone, propylene, ethylene, vinyl chloride, butadiene, methyl methacrylate, acrylic acid, 2-2-hydroxyethyl methacrylate, carbonate, and polyethylene terephthalate.

The hydrogel may include at least one selected from the group consisting of alginate, fibrinogen, carboxymethyl cellulose, heparan sulfate, hyaluronic acid, collagen, and dextran.

Figure 10:
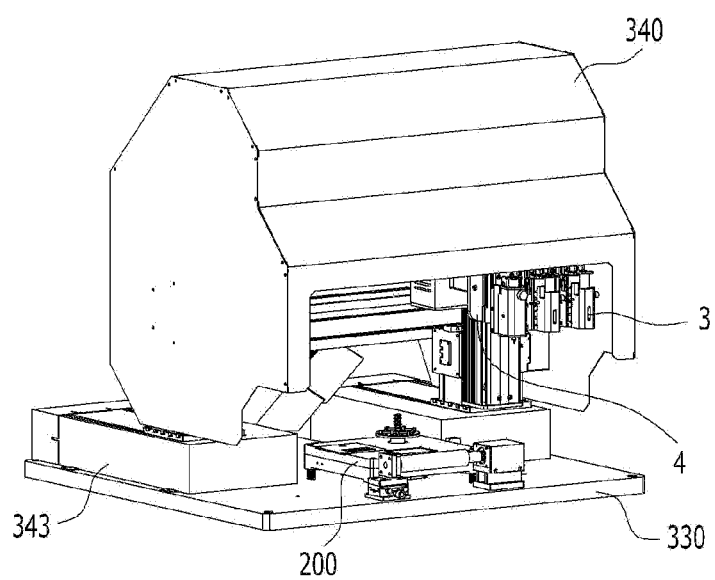
FIG. 10 is a perspective view illustrating an airflow guide coupled to the 3D printer according to the other embodiment of the present disclosure.
Figure 11:
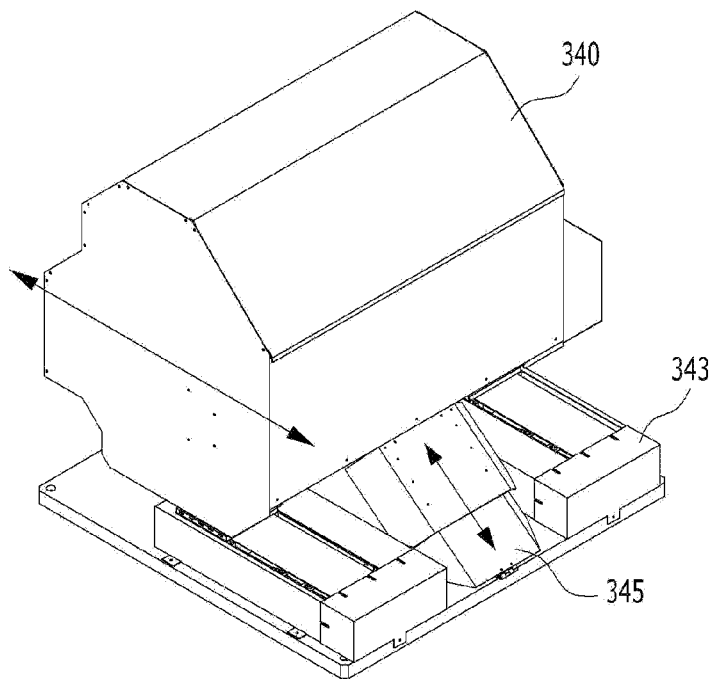
FIG. 11 is a rear view illustrating the airflow guide coupled to the 3D printer according to the other embodiment of the present disclosure.

FIG. 10 is a perspective view illustrating the airflow guide 340 coupled to the 3D printer 330, according to the other embodiment of the present disclosure. FIG. 11 is a rear view illustrating the airflow guide coupled to the 3D printer 330 according to the other embodiment of the present disclosure.

Referring to FIGS. 10 and 11, the airflow guide 340 prevents a backflow of air inside the housing 310 caused by the 3D printer 330 and controls an airflow, which is a flow of air supplied to the outside of the 3D printer 330 serving as the driving device, through the air supply unit 320, and is preferably formed in a structure that covers the 3D printer 330.

In detail, the airflow guide 340 is formed to cover a print head 3 and a head moving unit 4 of the 3D printer 330, and if necessary, may further include a stage cover 343 covering a stage 5 of the 3D printer 330 or a cable cover 345 covering a cable of the 3D printer 330. In this case, the cable cover 345 may be formed to slide through a rail structure or the like in conjunction with forward and backward movement of the airflow guide 340 (see FIG. 11).

Figure 12:
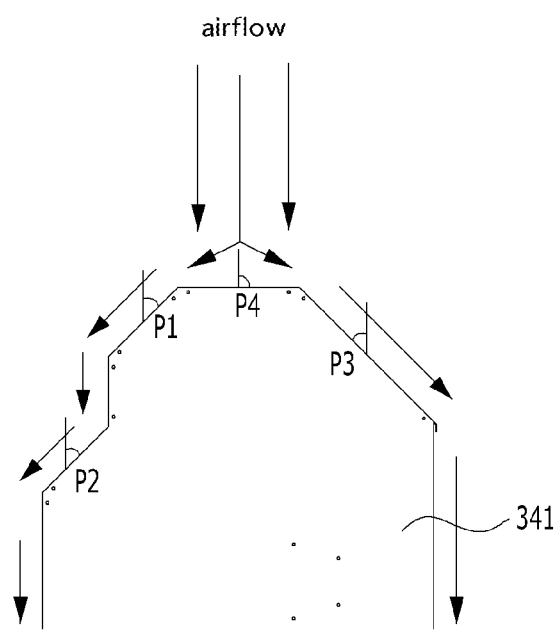
FIG. 12 is a side view illustrating the airflow guide coupled to the 3D printer according to the other embodiment of the present disclosure.

As illustrated in FIG. 12, surfaces constituting the airflow guide 340 may be formed to form an angle of equal to or less than 90 degrees with an inflow direction of airflow, and it is preferable that angles between the respective surfaces the and the airflow (P1, P2, P3, and P4 are illustrated in the drawings as examples, but are not limited thereto) are all equal to or less than 90° in a downward direction.

More preferably, the surfaces constituting the airflow guide 340 are all inclines surfaces not horizontal surfaces, and the angles (P1, P2, and P3 in FIG. 12) between the airflow and the respective inclined surfaces are all equal to or less than 90°. Even more preferably, the angles between the airflow and the inclined surfaces are all less than 90°. When considering the structure, shape, and size of the airflow guide 340, the angles may be set in the range of about 40° to 45°.

With such a structure of the airflow guide 340, the airflow, which is a flow of air supplied from an upper portion of the housing 310 through the air supply unit 320, can be effectively guided in the direction of the vent 313 formed in the lower portion of the housing 310, and fine particles inside the housing 310 can be effectively prevented from stagnating in a certain area to form a stagnant area.

As described above, the structure and shape of the airflow guide 340 surrounding the 3D printer, which is the driving device, has been mainly described, but the driving device is not limited to the 3D printer. The airflow guide 340 may be fixed in the clean bench to cover the driving device, and if necessary, the airflow guide 340 may be moved by an auxiliary means such as a rail.

A separate UV light source may be provided inside the housing 310. Because UV rays has a sterilizing power, the separate UV light source may be provided inside the housing 310 to irradiate an external region of the airflow guide 340 surrounding the 3D printer with UV rays, whereby the operation of the driving device (e.g., a 3D printing process) may be performed in an aseptic environment. The UV light source is preferably formed at a lower end of the air supply unit 320 so that the entire inner region of the housing 310 is evenly irradiated with UV rays.

In addition, as illustrated in FIG. 8, the clean bench system according to the present disclosure may further include a temperature and humidity adjustment unit 350 supplying air whose temperature and humidity are adjusted to the air supply unit 320. The temperature and humidity adjustment unit 350 includes: a casing 351 having an inlet 353 for allowing air to be introduced therethrough and an outlet 355 for allowing air to be discharged therethrough; a temperature control means provided inside the casing 351 to cool or heat air inside the casing 351; and a humidity control means provided inside the casing 351 to dehumidify or humidify the inside of the casing 351.

It is preferable that the inlet 353 is connected to the vent 313 of the housing 310 so that air discharged from the housing 310 is introduced into the temperature and humidity adjustment unit 350, and the outlet 355 is connected to the suction port 325 of the air supply unit 320 so that the air whose temperature and humidity are adjusted is supplied into the housing 310.

As described above, by continuously circulating the air having a constant temperature and humidity in the housing 310, temperature and humidity inside the housing 310 can be maintained constant.

Meanwhile, a clean bench system driving method according to another embodiment of the present disclosure relates to a method of using the above-described clean bench. The clean bench system driving method may include: a temperature and humidity control step of supplying air whose temperature and humidity are adjusted by a temperature and humidity adjustment unit 350 to an air supply unit 320; an air supply step of filtering the air supplied to the air supply unit 320 with a filter 323 and supplying the filtered air into a housing 310; and an air discharging step of discharging the air supplied to the inside of the housing 310 through a vent 313 formed in a lower portion of the housing 310. An airflow of the air supplied through the air supply unit 320 is controlled by an airflow guide 340 formed to cover a driving device located inside the housing 310.

Since the method and principle of controlling the airflow have already been described above, a detailed description thereof will be omitted herein.

The temperature and humidity control step is a step in which the temperature and humidity of the air inside a casing 351 are adjusted by the temperature control means and the humidity control means provided inside the casing 351, and the air whose temperature and humidity are adjusted is discharged to a suction port 325 of the air supply unit 320 through an outlet 355 and supplied to the air supply unit 320.

The air supply step is a step in which the air supplied to the air supply unit 320 is filtered through the filter 323 installed in an air supply port 321 and supplied into the housing 310. As the filter 323, a high efficiency particulate air filter (HEPA filter) or a pre-filter may be used, preferably a HEPA filter class EU10 having an efficiency of 95% to 99.9%, and more preferably a HEPA filter class U17 having an efficiency of 99.999995%.

Through the air supply step, the inside of the housing 310 is filled with a clean air whose temperature and humidity are adjusted, thereby providing a biologically stable and clean environment.

When a 3D printer 330 is provided as a driving device inside the housing 310 in which such a clean environment is provided, a jetting step of jetting a printing composition 1 through a print head 3 of the 3D printer 330 provided in the housing 310 may be performed. The printing composition 1 jetted through the print head 3 is stacked on a support plate 200 to form a 3D structure.

In this case, the 3D printer 330 is preferably coupled to the airflow guide 340 formed to cover the 3D printer 330. With such a structure in 30 and the 3D printer the airflow guide 340 are coupled to each other, a flow of air supplied from an upper portion of the housing 310 through the air supply unit 320 can be effectively guided in the direction of the vent 313 formed in the lower portion of the housing 310, and fine particles inside the housing 310 can be effectively prevented from stagnating in a certain area to form a stagnant area.

The printing composition 1 may include a thermoplastic polymer, a hydrogel, or a mixture thereof, and may further include cells in addition to the thermoplastic polymer or hydrogel if necessary.

The thermoplastic polymer may include, but is not limited to, for example, at least one selected from the group consisting of lactide, caprolactone, glycolide, dioxanone, propylene, ethylene, vinyl chloride, butadiene, methyl methacrylate, acrylic acid, 2-2-hydroxyethyl methacrylate, carbonate, and polyethylene terephthalate. The hydrogel may include at least one selected from the group consisting of alginate, fibrinogen, carboxymethyl cellulose, heparan sulfate, hyaluronic acid, collagen, and dextran.

When a bio 3D printing process is performed through the 3D printer 330 using a polymer, hydrogel, or a mixture thereof as the printing composition 1 as described above, the clean bench system according to the present disclosure is more useful because it can effectively remove not only physical and chemical pollutants but also biological pollutants.

The air discharging step is a step in which the air supplied into the housing 310 is discharged through the vent 313 formed in the lower portion of the housing 310. The vent 313 is preferably connected to an inlet 353 of the temperature and humidity adjustment unit 350 so that the discharged air is introduced into the temperature and humidity adjustment unit 350.

Figure 13:
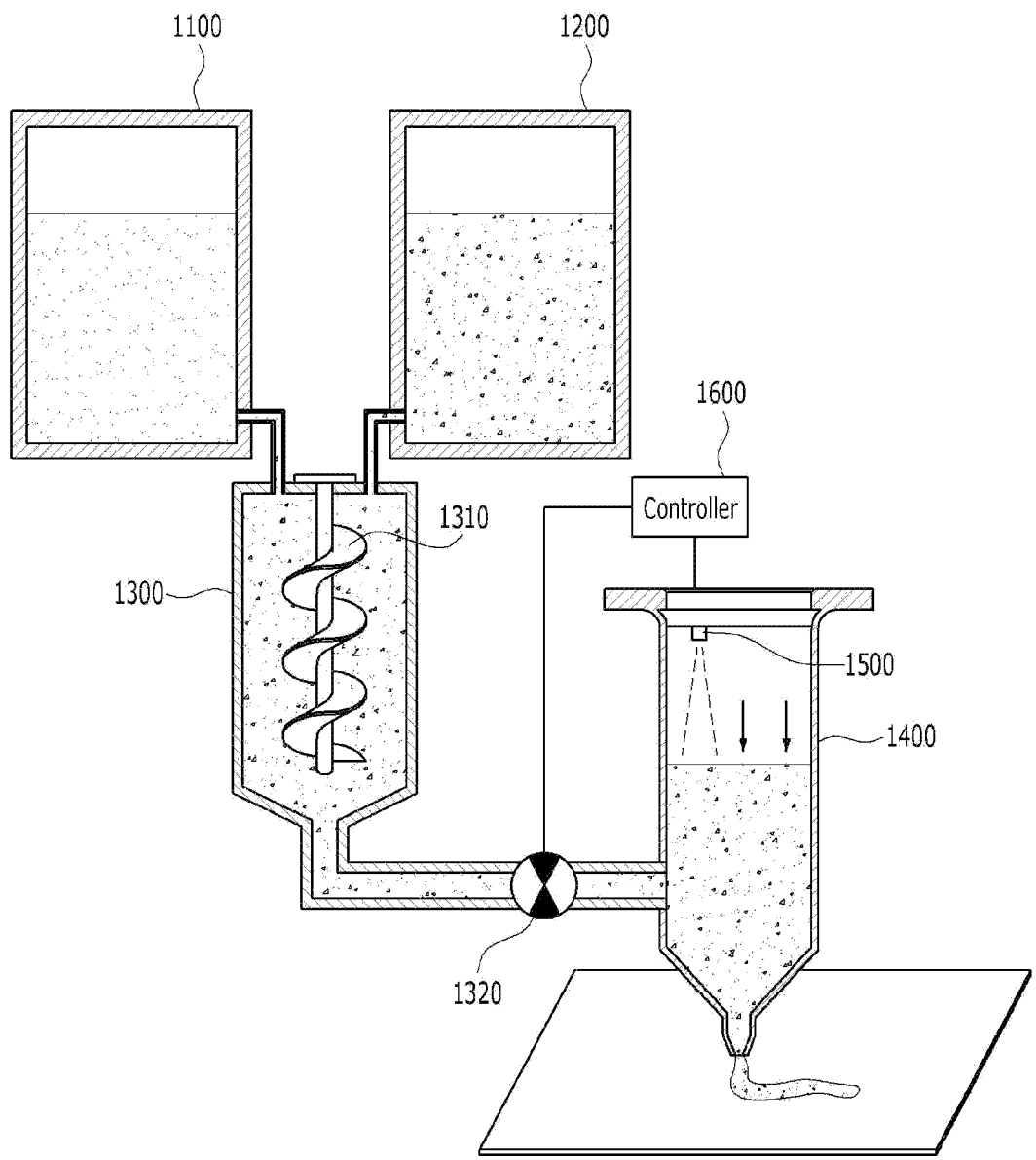
FIG. 13 is a conceptual diagram illustrating a schematic configuration of a bioink supply system according to another embodiment of the present disclosure.

Referring to FIG. 13, a bioink supply system according to another embodiment of the present disclosure may include: a hydrogel storage part 1100; cell storage part 1200; a mixing part 1300 receiving a hydrogel and cells from the hydrogel storage part 1100 and the cell storage part 1200; a sensor part 1500 measuring the level of bioink inside a syringe 1400; and a controller 1600 receiving a signal from the sensor part 1500 and maintain a constant level of the bioink inside the syringe 1400.

The hydrogel storage part 100 stores the hydrogel without a change in physical properties, and preferably has a structure blocked from the outside. The hydrogel may include, but is not limited to, a natural polymer material such as alginate, fibrinogen, carboxymethyl cellulose, heparan sulfate, hyaluronic acid, collagen, and dextran. Such hydrogels including collagen or alginate are suitable for use as bioinks due to a high water content and excellent biocompatibility thereof.

In order to store the hydrogel without a change in physical properties, the hydrogel storage part 1100 may include a temperature adjusting means and a pH adjusting means. The temperature adjusting means may be composed of a heating member such as a radiation heater, a convection heater, a conductive heater, etc. and a cooling member such as a radiation cooler, a convection cooler, a fan cooler, etc., and may maintain the inside of the hydrogel storage part 1100 at a temperature at which the hydrogel does not undergo gelation. In detail, when the hydrogel is collagen, it is preferable that the inside of the hydrogel storage part 1100 is maintained at a temperature of equal to or less than 15° C. through the temperature adjusting means.

In addition, the pH adjusting means of the hydrogel storage part 100 may be an automatic injector that receives a signal from a pH sensor for detecting a pH change provided in the hydrogel storage part 1100 and injects a basic solution into the hydrogel storage part 1100. The pH sensor measures the pH of the hydrogel stored in the hydrogel storage part 1100, determines an injection amount of the basic solution according to a change in pH, and sends a signal to the automatic injector to inject an appropriate amount of the basic solution, thereby maintaining the pH inside the hydrogel storage part 1100 in a pH range in which the hydrogel does not undergo gelation.

The hydrogel storage part 1100 is connected to the mixing part 1300 through a tube, and the hydrogel stored in the hydrogel storage part 1100 is supplied to the mixing part 1300 through a pump or the like.

The cell storage part 1200 stores a cell solution containing living cells, and preferably has a structure blocked from the outside. The conditions for cell survival and the conditions in which the hydrogel does not undergo gelation are different and thus, in order to store the cell solution containing live cells for a long period of time, the cell solution has to be stored separately from the hydrogel.

In order to store the cell solution containing the living cells, the cell storage part 1200 may include a regulator for maintaining a constant temperature, pH, and $CO_2$ concentration inside the cell storage part 1200. The regulator may be a regulator of a generally used incubator for cell culture, but is not limited thereto.

The inside of the cell storage part 1200 may be maintained under constant conditions of temperature, pH and $CO_2$ concentration for cell survival, and specifically, conditions of temperature of 37° C., pH of 7 to 7.5, and $CO_2$ concentration of 5% are preferably maintained.

The cell storage part 1200 is connected to the mixing part 300 through a tube, and the cell solution stored in the cell storage part 1200 is supplied to the mixing part 1300 through a pump or the like.

In order to prevent sedimentation of the cells in the cell storage part 1200, the cell storage part 1200 may include a stirring means. As the stirring means, a magnetic stirrer or a screw-type impeller may be used. In the case of using the stirring means as described above, it is possible to prevent cell sedimentation and maintain the concentration of the cells in the cell solution uniformly. Thus, a cell solution having a constant cell concentration can be supplied to the mixing part 1300.

The cells may be various cells, such as stem cells, fibroblasts, liver cells, etc. depending on the type of artificial tissue to be bioprinted.

The mixing part 1300 receives and mixes the hydrogel and the cell solution from the hydrogel storage part 1100 and the cell storage part 1200, respectively, and may include a mixing means 1310. The hydrogel and the cell solution are mixed to create bioink, and the bioink is supplied to the syringe 1400. The mixing means 1310 is preferably a mixing means 1310 capable of uniformly mixing the relatively high-viscosity hydrogel and the low-viscosity cell solution.

In an embodiment of the present disclosure, as the mixing means 1310, an impeller that is rotated by a separate power source may be used. As the separate power source, a motor may be used. The motor may be operated in conjunction with the impeller provided in the mixing part 1300 so that the impeller is strongly rotated by the motor, thereby effectively mixing the hydrogel and the cell solution.

In another embodiment of the present disclosure, as the mixing means, a magnetic stirrer may be used. The stirrer inside the mixing part 1300 may be rotated through a magnet disposed outside the mixing part 1300 to mix the hydrogel and the cell solution. In the case of using the magnetic stirrer, it is possible to mix the hydrogel and the cell solution inside the mixing part 1300 without mechanical contact, thereby preventing denaturation of the hydrogel and the cell solution.

The mixing part 1300 is connected to the syringe 1400 through a tube, and the bioink created in the mixing part 1300 is supplied to the syringe 1400 through a pump 1320 or the like.

The bioink supply system may include the sensor part 1500 measuring the level of the bioink inside the syringe 1400 and the controller 1600 receiving a signal from the sensor part 1500 and maintaining a constant level of the bioink inside the syringe 1400.

The sensor part 1500 measures the level of the bioink supplied to the syringe 1400 and transmits the measured value to the controller 1600. The controller 1600 maintains a constant level of the bioink inside the syringe 1400 by operating or stopping the pump 1320 for supplying the bioink to the syringe 1400 by comparing a set reference value with the measured value. In detail, when the measured value is equal to or less than the reference value, the controller 1600 operates the pump 1320 to supply the bioink to the syringe 1400 while the bioink is jetted from the syringe 1400, or stops the bioink from being jetted from the syringe 1400 and then operates the pump 1320 to supply the bioink to the syringe 1400. On the other hand, when the measured value is equal to or greater than the reference value, the controller 1600 stops the pump 1320 to stop the supply of the bioink, thereby maintaining a constant level of the bioink in the syringe 1400.

When the level of the bioink inside the syringe 1400 is maintained constant, the amount of the bioink jetted through the syringe 1400 during bioprinting can be maintained constant, thereby enabling precise bioprinting.

Figure 14:
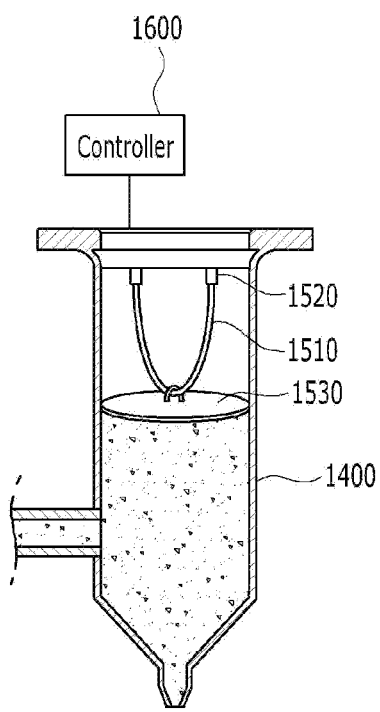
FIG. 14 is a view illustrating a sensor part of the bioink supply system according to the other embodiment of the present disclosure.

The sensor part 1500 may include a laser sensor as illustrated in FIG. 13 or a stretch sensor as illustrated in FIG. 14.

The stretch sensor 1510 is a sensor made of a flexible conductive rubber material and whose electrical resistance value changes as it is stretched and contracted. As illustrated in FIG. 14, each end of the stretch sensor 1510 may be connected to a sensor cable 1520 formed on an inner upper end of the syringe 1400. A cap 1530 may be connected to the stretch sensor 1510, so that as the cap 1530 is moved upwards and downwards according to the level of the bioink in the syringe 1400, the stretch sensor 1510 is stretched and contracted to measure the level of the bioink inside the syringe 1400 through a changed electrical resistance value.

In the case of using the stretch sensor 1510 as described above, it is possible to prevent the concentration of pneumatic pressure through the cap 1530, and to prevent a change in physical properties of the bioink by not allowing the stretch sensor 1510 to come into contact with the bioink.

Figure 15:
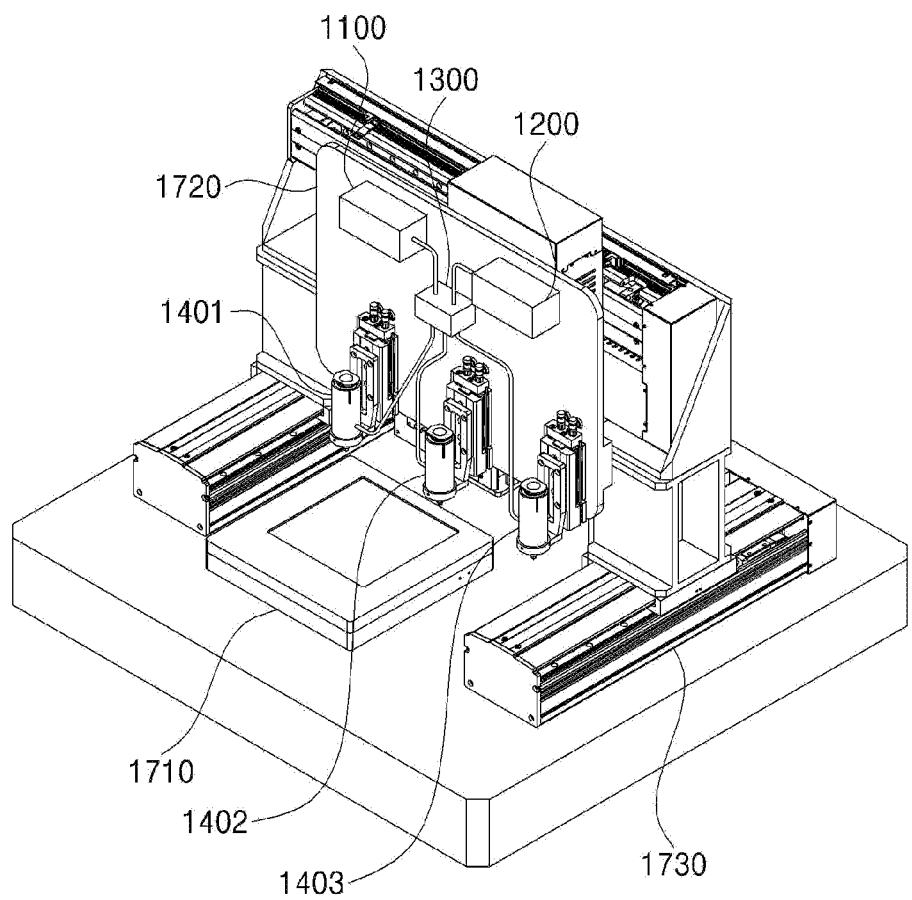
FIGS. 15 to 17 are perspective views each illustrating a 3D bioprinter to which a bioink supply system according to another embodiment of the present disclosure is applied.

As illustrated in FIG. 15, a bioink supply system according to an embodiment of the present disclosure may be applied a 3D bioprinter 1700 that jets bioink onto a support 1710 through syringes 1401, 1402, and 1403. A hydrogel storage part 1100, a cell storage part 1200, and a mixing part 1300 may be formed at a head moving unit 1720. The bioink may be supplied to each of the syringes 401, 402, and 403 from one mixing part 1300.

Figure 16:
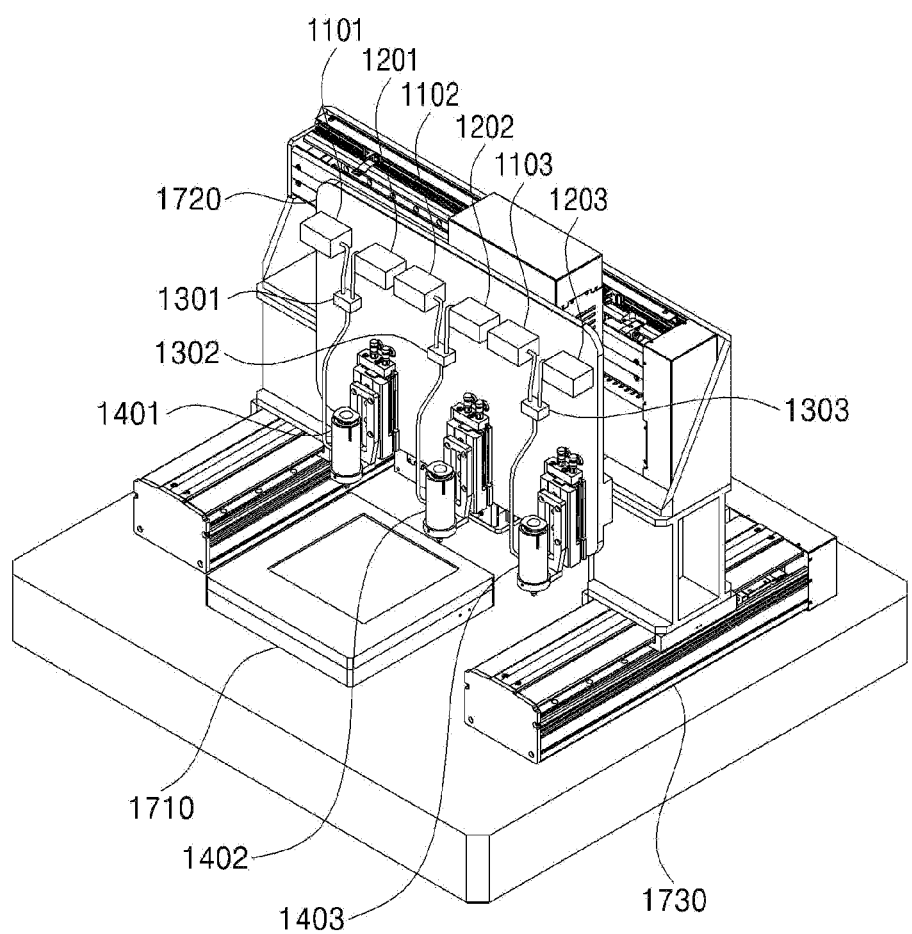

FIG. 16 is a perspective view illustrating a 3D bioprinter 1701 to which a bioink supply system according to another embodiment of the present disclosure is applied. Referring to FIG. 16, syringes 1401, 1402, and 1403 may be respectively connected to the hydrogel storage parts 1101, 1102, and 1103, cell storage parts 1201, 1202, and 1203, and mixing parts 1301, 1302, and 1303 that are formed at a head moving unit 1720. In this embodiment, it is possible to supply different types of bioinks to the respective syringe 1401, 1402, and 1403.

Figure 17:
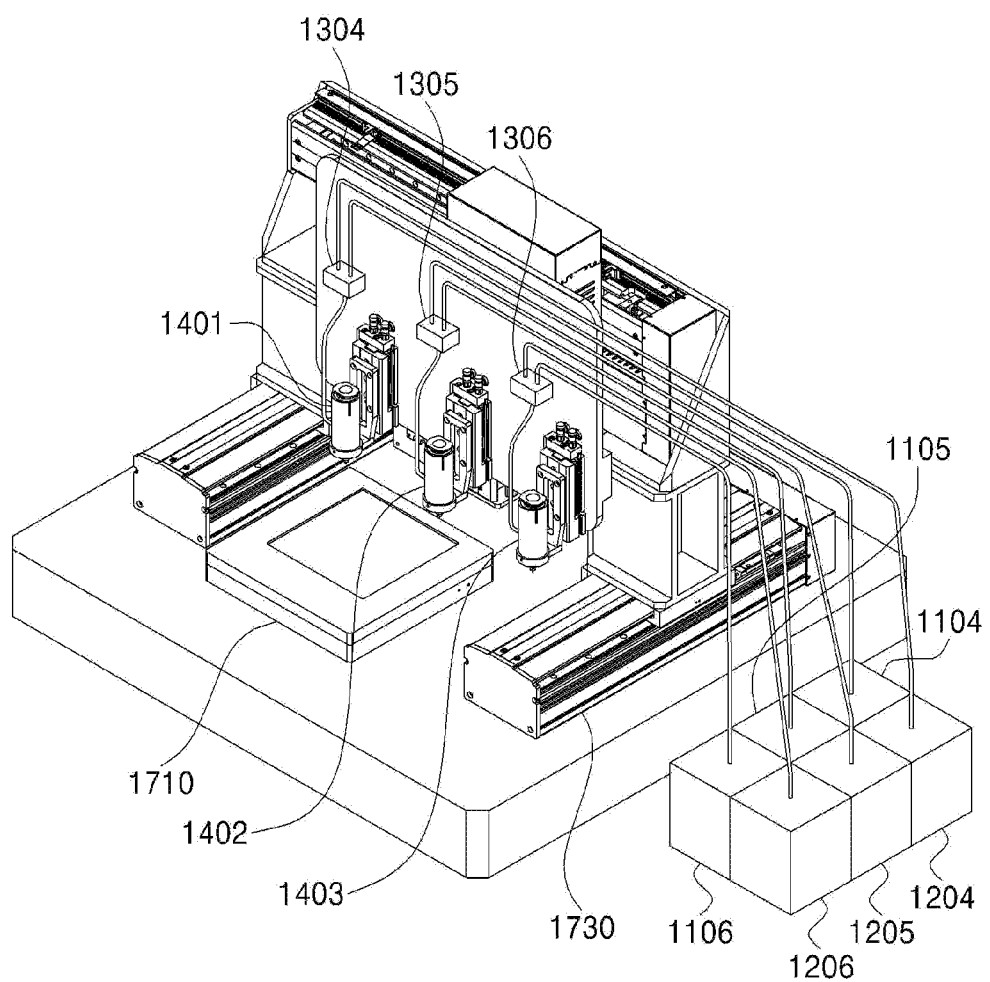

FIG. 17 is a perspective view illustrating a 3D bioprinter to which a bioink supply system according to another embodiment of the present disclosure is applied. In this embodiment, hydrogel storage parts 1104, 1105, and 1106 and cell storage parts 1204, 1205, and 1206 may be formed separately from a head moving unit 1720. Mixing parts 1304, 1305, and 1306 may receive a hydrogel and a cell solution from the separately formed hydrogel storage parts 1104, 1105, and 1106 and cell storage parts 1204, 1205, and 1206, respectively. As described above, in the case where the hydrogel storage parts 1104, 1105, and 1106 and the cell storage parts 1204, 1205, and 1206 are formed separately from the head moving unit 1720, it is possible to increase the capacity of the hydrogel storage parts 1104, 1105, and 1106 and the cell storage parts 1204, 1205, and 1206, thereby continuously supplying a larger amount of bioink to the syringes 1401, 1402, and 1403.

A 3D bioprinting method using the aforementioned bioink supply system according to another embodiment of the present disclosure may include: storing a hydrogel in a hydrogel storage part 1100; storing a cell solution in a cell storage part 1200; supplying the hydrogel and the cell solution from the hydrogel storage part 1100 and the cell storage part 1200 to a mixing part 1300; mixing the hydrogel and the cell solution in the mixing part 1300 and supplying the mixture to a syringe 1400; and maintaining a constant level of bioink inside the syringe 1400.

In the step of storing the hydrogel in the hydrogel storage part 1100, the hydrogel may include, but is not limited to, a natural polymer material such as alginate, fibrinogen, carboxymethyl cellulose, heparan sulfate, hyaluronic acid, collagen, and dextran.

When the hydrogel is collagen, the step of storing the hydrogel in the hydrogel storage part 1100 is preferably performed under conditions of temperature of 10° C. to 15° C. and pH of 5 to 6. When the above conditions are not satisfied, collagen undergoes gelation and thus cannot be used for 3D bioprinting.

The step of storing the cell solution in the cell storage part 1200 is preferably performed under conditions of $CO_2$ concentration of 5%, temperature of 37° C., and pH of 7 to 7.5 so that cells included in the cell solution can survive.

In addition, the step of storing the cell solution in the cell storage part 1200 may include stirring the cell solution in order to prevent sedimentation of the cells. As a means for stirring the cell solution, a magnetic stirrer or a screw-type impeller may be used.

In the step of mixing the hydrogel and the cell solution in the mixing part 1300 and supplying the mixture to the syringe 1400, the hydrogel and the cell solution are mixed to create bioink, and the bioink is supplied to the syringe 1400. As a mixing means 1310, an impeller or a magnetic stirrer may be used.

In the step of maintaining the constant level of the bioink inside the syringe 1400, the level of the bioink may be measured through a sensor part 1500, and the amount of the bioink supplied from the mixing part 1300 to the syringe 400 may be adjusted according to the measured value. As the sensor part 1500, a laser sensor or a stretch sensor may be used, but is not limited thereto.

When the measured value measured by the sensor part 1500 is equal to or less than a reference value, the bioink may be supplied to the syringe 1400 while being jetted from the syringe 1400, or the bioink may be stopped from being jetted from the syringe 1400 and then be supplied to the syringe 1400. On the other hand, when the measured value is equal to or greater than the reference value, the supply of the bioink may be stopped to maintain a constant level of the bioink in the syringe 400.

Experimental Example 2: Measurement of Printing Results According to Level of Bioink 3D bioprinting was performed under the same conditions such as pneumatic pressure and a syringe's moving speed, except for varying the level of bioink in the syringe to measure a jet amount of the bioink jetted from the syringe. The measurement results are illustrated in Table 1 below.

TABLE 1

| Bioink level (ml) | Jet amount (ml) |
| --- | --- |
| 2.0 | 0.069 ± 0.004 |
| 0.5 | 0.080 ± 0.001 |

As apparent from the results of Table 1, it was found that, when the level of the bioink in the syringe was 0.5 ml, the jet amount was about 17% more than when the level of the bioink was 2.0 ml. This means that the amount of the bioink jetted through the syringe during bioprinting varies according to the level of the bioink in the syringe. Thus, it will be seen that the level of the bioink in the syringe has to be maintained constant for precise bioprinting.

While the present disclosure has been described with reference to specific embodiments thereof, it will be apparent to those of ordinary skill in the art that various changes and modifications can be made therein without departing from the scope of the present disclosure as set forth in the claims below.

INDUSTRIAL APPLICABILITY

The present disclosure relates to a bioink supply system that can continuously supply an active bioink to a syringe of a bioprinter during 3D bioprinting, and to a three-dimensional (3D) bioprinting method using the same. By continuously supplying the active bioink to the syringe of the bioprinter, it is possible to continuously print large-scale biotissue, a plurality of organoids, organ-on-a-chip devices, etc. Also, it is possible to maintain a constant level of the bioink inside the syringe during bioprinting, thereby enabling precise bioprinting. Thus, the present disclosure has industrial applicability.

The invention claimed is:

1. A bioink supply system comprising:
   a hydrogel storage part;
   a cell storage part;
   a mixing part configured to receive and mix a hydrogel and a cell solution from the hydrogel storage part and the cell storage part;
   a sensor part configured to measure a level of bioink inside a syringe; and
   a controller configured to receive a signal from the sensor part and maintain a constant level of the bioink inside the syringe, wherein the mixing part supplies, to the syringe, the bioink prepared by mixing the hydrogel and the cell solution,
   wherein the cell storage part comprises a stirring means.

2. The bioink supply system of claim 1, wherein the hydrogel storage part comprises a pH adjusting means.

3. The bioink supply system of claim 1, wherein the cell storage part is maintained under conditions of $CO_2$ concentration of 5%, temperature of 37° C., and pH of 7 to 7.5.

4. The bioink supply system of claim 1, wherein the mixing part comprises an impeller as a mixing means.

5. The bioink supply system of claim 1, wherein the sensor part comprises a laser sensor or a stretch sensor.

6. A three-dimensional bioprinting method comprising:
   storing a hydrogel in a hydrogel storage part;
   storing a cell solution containing live cells in a cell storage part, which comprises a stirring means;
   supplying the hydrogel and the cell solution from the hydrogel storage part and the cell storage part to a mixing part; mixing
   the hydrogel and the cell solution in the mixing part and supplying the mixture to a syringe; and
   maintaining a constant level of bioink inside the syringe.

7. The three-dimensional bioprinting method of claim 6, wherein the hydrogel comprises alginate, fibrinogen, carboxymethyl cellulose, heparan sulfate, hyaluronic acid, collagen, or dextran.

8. The three-dimensional bioprinting method of claim 6, wherein the storing of the hydrogel is performed under conditions of temperature of 10° C. to 15° C. and pH of 5 to 6.

9. The three-dimensional bioprinting method of claim 6, wherein the storing of the cell solution is performed under conditions of $CO_2$ concentration of 5%, temperature of 37° C., and pH of 7 to 7.5.

* * * * *